(12) United States Patent
Kurfurst et al.

(10) Patent No.: US 8,409,633 B2
(45) Date of Patent: Apr. 2, 2013

(54) METHODS USEFUL IN STUDYING OR MODULATING SKIN OR HAIR PIGMENTATION, PLANT EXTRACTS FOR USE IN COMPOSITIONS AND COSMETIC CARE METHOD

(75) Inventors: Robin Kurfurst, Saint Jean de Braye (FR); Carine Nizard, Ivry sur Seine (FR); Sylvianne Schnebert, Olivet (FR); Eric Perrier, Les Cotes D'arey (FR); Desmond J. Tobin, West Yorkshire (GB); Suman K. Singh, Jharkhand Jamshedpur (IN)

(73) Assignee: L V M H Recherche, Saint Jean de Braye (FR)

( * ) Notice: Subject to any disclaimer, the term of this patent is extended or adjusted under 35 U.S.C. 154(b) by 0 days.

(21) Appl. No.: 13/063,150

(22) PCT Filed: Sep. 9, 2009

(86) PCT No.: PCT/EP2009/061712
§ 371 (c)(1),
(2), (4) Date: May 23, 2011

(87) PCT Pub. No.: WO2010/029115
PCT Pub. Date: Mar. 18, 2010

(65) Prior Publication Data
US 2011/0229431 A1 Sep. 22, 2011

(30) Foreign Application Priority Data

Sep. 10, 2008 (GB) .................................. 0816507.8
Jun. 12, 2009 (EP) ..................................... 09290446

(51) Int. Cl.
*A61K 36/00* (2006.01)
*A61K 8/97* (2006.01)
*A61K 36/48* (2006.01)
(52) U.S. Cl. ........................... 424/725; 424/74; 424/757
(58) Field of Classification Search .......................... None
See application file for complete search history.

(56) References Cited

FOREIGN PATENT DOCUMENTS

| EP | 1 514 536 A1 | 3/2005 |
|---|---|---|
| JP | 2003-095910 A | 4/2003 |
| WO | WO 97/34489 A1 | 9/1997 |
| WO | WO 2005/027946 A1 | 3/2005 |
| WO | WO 2006/037947 A1 | 4/2006 |
| WO | WO 2007/09430 A1 | 8/2007 |
| WO | WO 2007/098873 A1 | 9/2007 |
| WO | WO 2008/015342 A2 | 2/2008 |

OTHER PUBLICATIONS

International Search Report issued in application No. PCT/EP2009/061712 on Dec. 15, 2009.
Singh et al., "The silver locus product (Silv/gp100/Pmel17) as a new tool for the analysis of melanosome transfer in human melanocyte-keratinocyte co-culture," Experimental Dermatology, vol. 17, pp. 418-426, 2008.
Bohil et al., "Myosin-X is a molecular motor that functions in filopodia formation," PNAS, vol. 103, No. 33, pp. 12411-12416, Aug. 15, 2006.
Database WPI, Section Ch., Week 197321, Thomson Scientific, London GB, AN 1973-30029U, XP002557016, "Dermal cosmetic—contg an extract from green barley or rye," & JP 48 015616 B, (Hagihara, Y.), May 16, 1973, abstract.
Sousa et al., "Myosin-X: a molecular motor at the cell's fingertips," Trends in Cell Biology, vol. 15, No. 10, pp. 533-539, Oct. 2005.
Snyder et al., "Classification of the Solvent Properties of Common Liquids," Journal of Chromatography, vol. 92, pp. 223-230, 1974.
Scott et al., "Filopodia are conduits for melanosome transfer to keratinocytes," J. Cell Science, vol. 115, pp. 1441-1451, 2002.
Kawabata et al., "Signal Transduction by Bone Morphogenetic Proteins," vol. 9, No. 1, pp. 49-61, 1998.
Lucas Meyer Cosmetics, "Whitessence lightening concentrate," Online, http://www.dcingredients.com/images/WHITESSENCE_-_Brochure.pdf, Nov. 20, 2009.

*Primary Examiner* — Qiuwen Mi
(74) *Attorney, Agent, or Firm* — Foley & Lardner LLP

(57) ABSTRACT

The invention relates to methods useful in studying or modulating skin or hair pigmentation and to the use of plant extracts in compositions as well as to methods comprising the topical use of such compositions to reduce or to enhance skin or hair pigmentation.

7 Claims, 8 Drawing Sheets

SEQUENCE LISTING

<160> NUMBER OF SEQ ID NOS: 1

<210> SEQ ID NO 1
<211> LENGTH: 21
<212> TYPE: DNA
<213> ORGANISM: Homo sapiens

<400> SEQUENCE: 1
cagcggtata agagaaatca a                                                 21

METHODS USEFUL IN STUDYING OR MODULATING SKIN OR HAIR PIGMENTATION, PLANT EXTRACTS FOR USE IN COMPOSITIONS AND COSMETIC CARE METHOD

The present invention relates to methods useful in studying or modulating skin or hair pigmentation, to the use of plant extracts, as active agents modulating melanin skin or hair pigmentation for the preparation of compositions and to cosmetic care method.

In humans, pigmentation results from the synthesis and distribution of melanin pigments in the skin, the hair follicles or the eyes. Pigmentation is genetically predefined, but it is regulated by numerous internal or external factors. The melanins produced by melanocytes and also the number of melanocytes, their tyrosinase activity and their ability to export melanins to keratinocytes, and the size of the melanosomes which contain melanin granules, will condition the colour of human skin. For each individual, the colour of the skin varies mainly according to how much or how little irradiation it receives from ultraviolet (UV) rays. In other words, for each individual, there is a basic skin pigmentation when said individual is subjected to the weakest UV irradiation, corresponding to his or her lightest skin colour, and a more intense skin pigmentation if he or she receives a stronger UV irradiation, ranging up to the maximum pigmentation corresponding to his or her darkest skin colour when subjected to sustained exposure to intense UV irradiation.

Furthermore, as is well known, a very large genetic diversity with regard to skin pigmentation exists in the worldwide population. Thus, according to populations, the skin colour corresponding to the basic pigmentation defined above has a darker or lighter shade which lies between the two extremes: very light and very dark. Also according to populations, the difference in skin shade between the basic pigmentation and the maximum pigmentation is more or less great. Thus, it is well known that individuals belonging to certain populations with light skin (basic pigmentation) react rapidly and/or considerably to the action of UV radiation and can therefore readily exhibit skin with a dark shade, even when these individuals have not intentionally exposed themselves to the sun for a prolonged period.

Moreover, individuals experience the appearance on their skin, in particular on the face or the hands, of areas and/or spots which are darker and/or more coloured, conferring a colour heterogeneity on the skin. These spots are due to a large concentration of melanin in the epidermal keratinocytes resulting from an exacerbated melanogenic activity in the melanocytes.

The mechanism of formation of skin pigmentation involves the synthesis of melanins. This mechanism is particularly complex and involves, schematically, the following main steps:

Tyrosine→Dopa→Dopaquinone→Dopachrome→Melanins

Tyrosinase and tyrosinase-related-protein 1 (TRP-1) are essential enzymes involved in this series of reactions. They catalyse in particular the reaction for conversion of tyrosine to Dopa (dihydroxyphenylalanine) and the reaction for conversion of Dopa to Dopaquinone, resulting in the formation of melanin pigments.

A molecule is recognized to be a depigmenting molecule if it acts directly on the epidermal melanocytes by inhibiting the activity of these cells and/or if it blocks one of the steps of melanin biosynthesis or else if it degrades the melanin formed. This is in particular the case when the molecule inhibits one of the enzymes involved in melanogenesis or when it reacts with the chemical compounds of the melanin synthesis chain.

Known depigmenting substances are in particular hydroquinone and derivatives thereof, kojic acid, arbutin, iminophenols, the combination of carnitine and quinone, aminophenol amide derivatives, and benzothiazole derivatives. These substances can have certain drawbacks. They can be unstable, can require use at high concentrations, can lack specificity with regard to their method of action, or can have a cytotoxic or irritant capacity.

On the other hand, a molecule is recognized to be pigmenting molecule by its stimulating activity on melanogenesis in the melanocytes present in the skin or the hair follicles, and thus making possible to promote the pigmentation of the skin or hair as well as to treat disorders of the pigmentation of the skin and hair, more particularly by promoting the biosynthesis of melanin.

Known pigmenting substances are in particular adenylate cyclase activators such as forskoline (*Coleus forskholii* extract) or *Tephrosia purpurea* extract.

Melanocytes are neural crest-derived cells distributed along the basal layer of the epidermis and hair bulb. These cells synthesize melanin pigment through a process called melanogenesis within unique melanocyte-specific organelles called melanosomes. For skin and hair to become pigmented this melanin must be transferred from melanocytes to adjacent keratinocytes. Mammalian skin eyes, and hair/wool/fur colour is determined by melanin quantity and quality (brown/black eumelanin or red/yellow pheomelanin) in a process that involves a large number of steps regulated at multiple control points by a range of different molecules and compounds. The last couple of decades have seen much progress in our understanding of the molecular control of melanin synthesis and melanosome biogenesis/maturation.

However the knowledge on how melanin transfer is controlled would have a primary clinical/cosmetic interest as this process ultimately controls the level of pigmentation perceived at the skin surface and along the hair fiber.

The inventors have shown the mechanism that controls melanin transfer from human cutaneous melanocytes to human cutaneous keratinocytes involving the action of myosin X (Myo-X), which regulates the transfer of melanin from melanocytes to keratinocytes.

The involvement of Myo-X in melanocyte biology (e.g, melanin transfer) has not been reported so far. While much is known about the regulation of melanogenesis (i.e. melanin synthesis) in melanocytes, the knowledge of how melanosomes transfer from melanocytes to keratinocytes is still very limited. In addition to a role for cyto-phagocytosis, there is increasing evidence to support melanosome transfer via filopodia which can interact with keratinocyte plasma membrane (Scott et al., 2002, Singh et al., 2008). Importantly structures consistent with filopodia arising from the sides and tips of melanocyte dendrites and which contain melanosomes within their lumina, have already been reported in human skin in situ as well as in vitro (Scott et al., 2002).

During studies on the biology of melanin transfer the present inventors investigated the potential role of a Myo-X in this process. In this application a novel mechanism that controls melanin transfer from human cutaneous melanocytes to human cutaneous keratinocytes is described.

This mechanism involves the action of Myo-X. Myo-X regulates the production of nanotubules (called filopodia) on melanocytes, which act as intercellular conduits for melanin transfer. To provide evidence that Myo-X regulates melanin transfer we used gene-silencing technology to knockdown its expression in melanocytes. Lack of Myo-X resulted in the loss of melanocyte filopodia and the concomitant inhibition of melanosome transfer to keratinocytes.

The present inventors have examined how filopodia production is regulated and have observed that actin-based motor proteins of the myosin superfamily may be involved. Specifically, Myosin-X (Myo-X)—a 240 KDa vertebrate-specific MyTH4-FERM myosin—is critical for filopodia formation (Sousa and Cheney 2005). It functions as part of a filopodial tip complex and/or by transporting molecules required for filopodia formation (Bohil et al., 2006).

In this application it is reported for the first time that Myo-X can control melanin transfer between human melanocytes and human keratinocytes. Myo-X and molecules based on its structure and action can be used as a novel regulation of mammalian skin and hair pigmentation.

According to a first aspect, the present invention provides a method of assessing the ability of a substance to modulate the transfer of melanin from a melanocyte to a keranocyte, the method comprising the step of:
 a)—providing a test substance;
 b)—providing a cell expressing Myo-X;
 c)—determining the ability of the test substance to modulate the expression or the activation of Myosin-X (Myo-X).

"Modulating" means that the active agent is able either to increase the expression or the activity of Myo-X or to decrease the expression or the activity of Myo-X in humans, this active agent acting either directly on Myo-X or indirectly, i.e. on an upstream target in the Myo-X metabolic pathway.

Preferably the cell expressing Myo-X is a melanocyte or a keratinocyte, more preferably a melanocyte.

The method of assessing the ability of a substance to modulate the transfer of melanin according to the present invention comprises comparing the expression or activation of Myo-X in a cell treated with a test substance with the expression or the activation of Myo-X in a control cell.

Determining said ability includes:
 measuring the amount of Myo-X protein in or on the cell;
 determining the amount of a precursor in the synthesis of Myo-X protein; or
 measuring the melanosome transfer level in the cell.

Methods for determining the expression of Myo-X include measuring the amount of Myo-X protein in or on the cell, or determining the amount of a precursor in the synthesis of Myo-X protein, for example mRNA which codes for Myo-X. Techniques required to determine the level of expression of Myo-X protein or Myo-X mRNA levels would be apparent to the person skilled in the art. Techniques to determine protein levels may involve immunostaining, ELISA, two-dimensional electrophoresis or mass-spectrometric methods. Techniques to determine mRNA levels might involve northern blotting, reverse transcriptase PCR, quantitative PCR, microarrays or Affymetrix® chips.

The level of expression or activation of Myo-X may be determined by many methods apparent to the person skilled in the art. In embodiments of the present invention the expression may be determined using immunofluorescence, western blotting or by determining the level of Myo-X mRNA. As mentioned above, other suitable methods would be apparent to the person skilled in the art.

Methods for determining the activity of Myo-X include measuring the melanosome transfer level in a cell. Techniques required to determine such level may involve the quantitative analysis of the melanin transfer to keratinocytes and would be apparent to the person skilled in the art.

Techniques to determine melanin transfer level may involve the use of gp100 as molecular tracker such as describes by Singh S K et al., Exp. Dermatol. 17, 5, 418-426 or any suitable methods apparent to the person skilled in the art.

According to other aspects, the present invention provides a method of selecting an active substance capable to enhance skin or hair pigmentation comprising:
 assessing the ability of said substance to modulate the transfer of melanin according to steps a) to c) of the method of claim 1,
 selecting the substance capable to increase the expression or the activation of Myo-X and a method of selecting a substance capable to reduce skin or hair pigmentation comprising:
 assessing the ability of said substance to modulate the transfer of melanin according to steps a) to c) of the method of claim 1,
 selecting the substance capable to decrease the expression or the activation of Myo-X.

In the sense of the present invention, "skin or hair pigmentation" has to be understood as "skin or hair pigmentation in humans".

According to the present invention, the assessed or test substance is a plant extract. The plant extract selected by the method of the invention as being capable to increase the expression or the activation of Myo-X is chosen in the group consisting of an extract of soybean, preferably a soy seed extract, more preferably a soy seed pericarp extract and the plant extract selected by the method of the invention as being capable to decrease the expression or the activation of Myo-X is chosen in the group consisting of: an extract of *Artocarpus* genus plant, preferably a *Artocarpus heterophyllus* extract, more preferably a *Artocarpus heterophyllus* seed extract; an extract of *Cyathea* genus plant, preferably a *Cyathea cumingii* extract more preferably a *Cyathea cumingii* leaf extract; an extract of *Secale* genus plant, preferably a *Secale cereale* extract, more preferably a *Secale cereale* seed extract; an extract of *Thalassiosira* genus plant, preferably the secretion of *Thalassiosira pseudonana* and an extract of *Buddleja* genus plant, preferably a *Buddleja axillaris* extract, more preferably a *Buddleja axillaris* leaf extract.

According to another aspect, the present invention provides the use of at least one of the above plant extract in a cosmetic composition, or in the preparation of a cosmetic composition as an active agent modulating the expression or the activity of Myo-X, said composition being intended to modulate skin or hair pigmentation.

According to the present invention, the plant extract can be prepared by various extraction processes known to a person skilled in the art.

The extraction is preferably performed by placing the plant material selected in contact with a polar solvent or a mixture of polar solvents. According to this invention, the term "polar solvent" means that the solvent has a polarity index value equal to or greater than a value of 4. The polarity index is a quantity calculated on the basis of thermodynamic quantities (of solubility and change in state) indicating the more or less polar nature of a molecule.

Reference can be made, for the solvent polarity indices, to the article of L. R. SNYDER: Classification of the solvent properties of common liquids; Journal of Chromatography, 92 (1974), 223-230, which is included by reference to this application.

The polar solvent is advantageously chosen from water, C1-C4 alcohols, such as ethanol, glycols, ethylene glycol, glycerol, butyleneglycol and propyleneglycol and mixtures thereof.

Preferably, the extraction is performed by using a hydro-alcoholic mixture, in particular a water-ethanol mixture, and preferably a water-ethanol mixture, advantageously in a 50/50 (v/v) ratio.

According to the present invention, the at least plant extract capable to modulate the expression or the activity of Myo-X is chosen in the group consisting of an extract of *Artocarpus* genus plant, preferably a *Artocarpus heterophyllus* extract, more preferably a *Artocarpus heterophyllus* seed extract; an extract of *Cyathea* genus plant, preferably a *Cyathea cumingii* extract, more preferably a *Cyathea cumingii* leaf extract; an extract of *Secale* genus plant, preferably a *Secale cereale* extract more preferably a *Secale cereale* seed extract; an extract of *Thalassiosira* genus plant, preferably the secretion of *Thalassiosira pseudonana*; an extract of *Soybean* genus plant, preferably a soy seed extract, more preferably a soy seed pericarp extract; an extract of *Buddleja* genus plant, preferably a *Buddleja axillaris* extract more preferably a *Buddleja axillaris* leaf extract.

In particular, an extract of *Artocarpus* genus plant, preferably a *Artocarpus heterophyllus* extract, more preferably a *Artocarpus heterophyllus* seed extract; an extract of *Cyathea* genus plant, preferably a *Cyathea cumingii* extract more preferably a *Cyathea cumingii* leaf extract; an extract of *Secale* genus plant, preferably a *Secale cereale* extract, more preferably a *Secale cereale* seed extract; an extract of *Thalassiosira* genus plant, preferably the secretion of *Thalassiosira pseudonana*; an extract of *Buddleja* genus plant, preferably a *Buddleja axillaris* extract, more preferably a *Buddleja axillaris* leaf extract are active agents decreasing the expression or the activity of Myo-X and an extract of soybean, preferably a soy seed extract, more preferably a soy seed pericarp extract, is an active agent increasing the expression or the activity of Myo-X.

Another object of the present invention is to provide at least a plant extract chosen in the group consisting of an extract of *Cyathea* genus plant, preferably a *Cyathea cumingii* extract more preferably a *Cyathea cumingii* leaf extract; an extract of *Secale* genus plant, preferably a *Secale cereale* extract, more preferably a *Secale cereale* seed extract; an extract of *Thalassiosira* genus plant, preferably the secretion of *Thalassiosira pseudonana*; an extract of soybean, preferably a soy seed extract, more preferably a soy seed pericarp extract, for the use in a cosmetic composition, or in the preparation of the cosmetic composition as an active agent modulating the skin or hair pigmentation in particular, an extract of *Cyathea* genus plant, preferably a *Cyathea cumingii* extract more preferably a *Cyathea cumingii* leaf extract; an extract of *Secale* genus plant, preferably a *Secale cereale* extract, more preferably a *Secale cereale* seed extract; an extract of *Thalassiosira* genus plant, preferably the secretion of *Thalassiosira pseudonana*; are active agents for use to reduce the skin or hair pigmentation and an extract of soybean, preferably a soy seed extract, more preferably a soy seed pericarp extract is an active agent for use to enhance the skin or hair pigmentation.

According to another aspect of the present invention there is provided a cosmetic care method comprising the topical use of a cosmetic composition comprising at least one plant extract chosen in the group consisting of an extract of *Cyathea* genus plant, preferably a *Cyathea cumingii* extract more preferably a *Cyathea cumingii* leaf extract; an extract of *Secale* genus plant, preferably a *Secale cereale* extract, more preferably a *Secale cereale* seed extract; an extract of *Thalassiosira* genus plant, preferably the secretion of *Thalassiosira pseudonana*; an extract of soybean, preferably a soy seed extract, more preferably a soy seed pericarp extract, in order to reduce or to enhance skin or hair pigmentation.

According to a further aspect of the present invention there is provided a cosmetic care method comprising the topical use of a cosmetic composition comprising at least one plant extract, obtainable by the methods of the invention as active agent modulating the expression or the activity of Myo-X in order to reduce or to enhance skin or hair pigmentation.

In particular, an extract of *Cyathea* genus plant, preferably a *Cyathea cumingii* extract more preferably a *Cyathea cumingii* leaf extract; an extract of *Secale* genus plant, preferably a *Secale cereale* extract, more preferably a *Secale cereale* seed extract; an extract of *Thalassiosira* genus plant, preferably the secretion of *Thalassiosira pseudonana* are active agents reducing skin pigmentation and an extract of soybean, preferably a soy seed extract, more preferably a soy seed pericarp extract, are active agents enhancing skin or hair pigmentation.

According to the present invention, the at least plant extract as described above is used to prepare a cosmetic composition or is used as an active agent modulating skin or hair pigmentation in the preparation of cosmetic composition lightening or darkening the skin or hair pigmentation.

According to the present invention, the above plant extracts are used at concentrations range, expressed in dry weight, between 0.0001% and 10% by weight of the composition of the invention, and preferably between 0.01% and 2%.

According to another aspect, the present invention provides a cosmetic care method wherein a cosmetic composition comprising an active substance modulating the expression or the activity of Myo-X is typically used to reduce or to enhance skin or hair pigmentation.

In a preferred embodiment said active substance is a nucleic acid, more preferably a RNA molecule, capable of modulating the expression of Myo-X through interaction with DNA or RNA coding for Myo-X or a functional portion thereof.

In particular, said RNA molecule is capable of targeting anti-sense interaction or RNA interference against mRNA encoding Myo-X.

In one embodiment, said RNA molecule is an mRNA molecule for targeting Myo-X mRNA via RNAi having the sequence 5'-CAGCGGTATAAGAGAAATCAA-3'(SEQ ID No 1).

It is within the skills of the person skilled in the art to determine other suitable sequences which would exhibit RNAi against Myo-X mRNA.

The cosmetic or pharmaceutical compositions, especially dermatological compositions according to the present invention, have thus a variety of applications in cosmetology or dermatology not only where it is desired to reduce the pigmentation but also where it is desired to enhance the pigmentation.

For example, these depigmenting compositions can be used for obtaining a lightening effect of the human skin or for obtaining a homogeneous skin colour. They can also be used in case of appearance on the skin, in particular on the face or the hands, of areas and/or spots which are darker and/or more colored, conferring a colour heterogeneity on the skin. These spots are due to a large concentration of melanin in the epidermal keratinocytes resulting from an exacerbated melanogenic activity in the melanocytes. Said compositions are in particular used for treated regional hyperpigmentations due to melanocyte hyperactivity, such as idiopathic melasmas, localized hyperpigmentations due to melanocyte hyperactivity, such as pigmentary spots referred to as solar lentigo or senile lentigo, accidental hyperpigmentations such as photosensitization or post-lesional cicatrization, and also certain forms of leucoderma such as vitiligo. In the latter cases, since it is not possible to repigment the skin, the pigmentation at the periphery of the depigmented zones is reduced so as to give the skin a more homogeneous colour.

In a preferred embodiment of the present invention, cosmetic compositions comprising at least plant extracts capable of reducing the skin or hair pigmentation (chosen in the group consisting of an extract of *Cyathea* genus plant, preferably a *Cyathea cumingii* extract more preferably a *Cyathea cumingii* leaf extract; an extract of *Secale* genus plant, preferably a *Secale cereale* extract, more preferably a *Secale cereale* seed extract; and an extract of *Thalassiosira* genus plant, preferably the secretion of *Thalassiosira pseudonana*) are used in a cosmetic care method for the cosmetic treatment of skin or hair hyperpigmentations including those associated with diseases such as: idiopathic melasmas, lentigo. Said compositions are also used in a cosmetic care treatment for cosmetically reducing pigmentation contrasts as being the consequence of a depigmented area surrounded by normally or more pigmented skin, such in the case of vitiligo.

Depigmenting compositions according to the present invention are also used as skin-bleaching agents by certain individuals, in particular those who are very reactive to UV radiations, so as to lighten their colouring, in particular that of their face and their hands, in order to maintain a skin colour which is a slight as possible or at the very least to reduce the pigmenting effects of UV rays.

On the other hand, the pigmenting compositions according to the present invention can be used as sun products to accelerate or intensify tanning, which apart from the esthetic advantage often sought, enables the natural defenses against ultra violet radiations to be strengthened by increasing the proportions in melanin in the epidermis. These compositions can also be used, for example in a form of creams, to give the skin a more sunburnt appearance, or else in the form of lotions to prevent and treat the appearance of gray hair.

In a preferred embodiment of the present invention cosmetic compositions comprising at least plant extracts capable of enhancing the skin or hair pigmentation (chosen in the group consisting of an extract of soybean, preferably a soy seed extract, more preferably a soy seed pericarp extract) are used in a cosmetic care method for the cosmetic treatment of skin or hair depigmentations including those associated with diseases such as: tinea versicolor, pityriasis alba, lupus erythematosus, mycosis fungoides, sarcoidosis, leprosy, syphilis and nevus depigmentosus.

Furthermore the cosmetic compositions according to the present invention may include, in addition to the at least plant extract, any other active agent modulating or not skin or hair pigmentation such as sunscreens and may also include at least one cosmetically acceptable excipient which can be chosen from polymers, surfactants, rheology control agents, fragrances, electrolytes, pH adjusters, antioxidants, preservatives, dyes, mother-of-pearl, pigments and mixtures thereof.

The cosmetic compositions referred to in the present invention are intended for topical use. These compositions can for example be a serum, a lotion, a spray, a foam, a solution, a powder, a pomade, a milk, an emulsion, a tinted cream or a hydrogel, and can be in the form of a stick, a patch or a mask.

Moreover, the cosmetic compositions according to the present invention, intended for topical administration, can contain at least one agent for promoting penetration and diffusion in the cutaneous structures in question, such as the agents commonly used in the fields of cosmetology and dermopharmacy, for example glycerol, propylene glycol, oleic acid or essentials oils, especially menthol and eucalyptol.

Embodiments of the present invention will now be described, by way of example only, with reference to the accompanying drawings in which.

BACKGROUND

Figure 1:
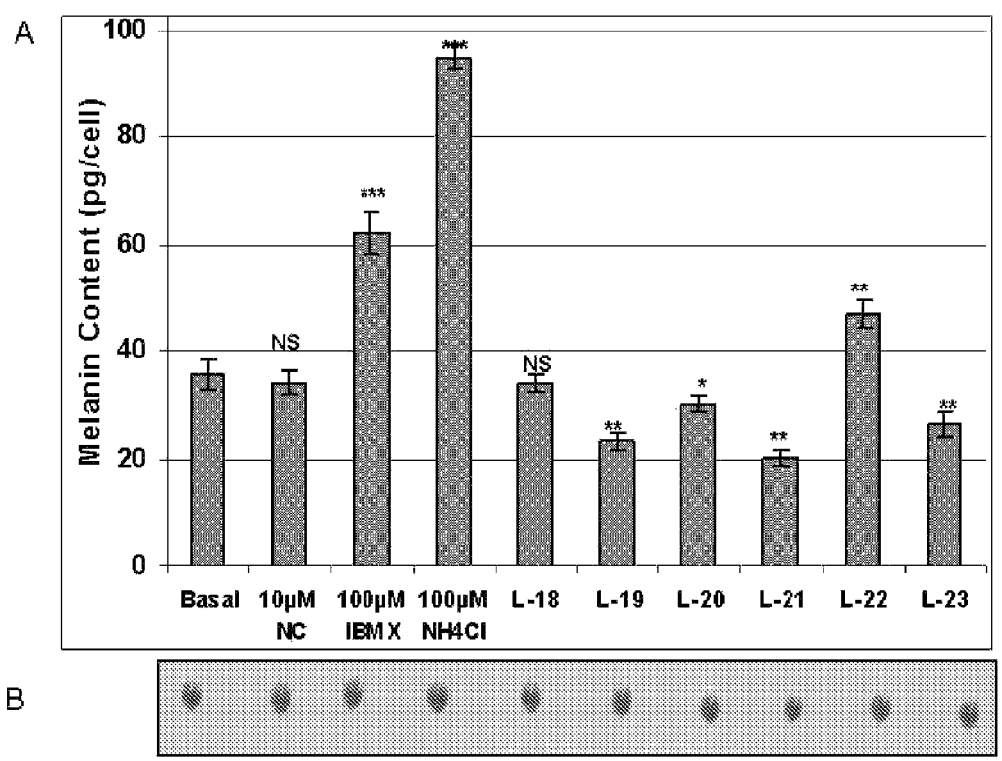
FIG. 1 shows the effect of plant extracts of the invention actives on melanogenesis in normal pigmented human melanocytes.

On the results reported below the plant extracts used according to the present invention are identified by their respective original coded name, with the following correspondence:

L-18: *Artocarpus heterophyllus* seed extract,
L-19: *Cyathea cumingii* leaf extract (polar solvent extraction),
L-20: *Secale cereale* seed extract (polar solvents extraction, in particular water, followed by an enzymatic hydrolysis),
L-21: Secretion of *Thalassiosira pseudonana* (obtained from a culture in sea water),
L-22: Soy seed pericarp extract (aqueous suspension followed by an enzymatic hydrolysis),
L-23: *Buddleja axillaris* leaf extract (extraction/concentration, then lyophilisation/sterilisation).

This report presents data on the effect of various L-18-23 on melanosome transfer in normal human epidermal melanocytes to fully matched epidermal keratinocytes.

The optimal doses have been standardized for each plant extract active separately on epidermal melanocytes and keratinocytes. The effect of all L-18-23 on a) melanin synthesis and b) tyrosinase activity using melanocytes cultured alone and cultured together with matched keratinocytes (i.e., EM-KC co-cultures) has been assessed. The effects of the plant extracts actives on melanosome transfer in EM: KC co-culture using gp00 immunolabelling has been evaluated.

Both positive melanocyte modulator (IBMX) and a melanosome transfer inhibitor (Niacinamide) were used as control for this study.

In general, L-18, 19, 20, 21, 23 downregulated melanin synthesis, dopa-oxidase activity of tyrosinase, melanosome transfer, and Myo-X expression. In fact, L-18 and L-23 were known as depigmentating agents but their action on these parameters was not shown so far. By contrast, L-22 was found to upregulate said parameters.

Materials & Methods

Stimulation of Melanocytes and Melanoma Cells with Plant Extracts of the Invention.
Cell Culture:
In the report below, the starting material used
for L-18, is a powder (put in aqueous mother solution, then adjusted to the indicated concentration),
for L-19, is a solution in a water/glycerol mixture at dry extract 30%,
for L-20, is an aqueous solution at dry extract 5.6%,
for L-21, is an aqueous solution at dry extract 6%,
for L-22, is an aqueous solution at dry extract 15%,
for L-23, is a powder (put in aqueous mother solution, then adjusted to the indicated, concentration),
Assessment of doses: Fully-matched epidermal melanocytes EM and epidermal keratinocytes (EK) were seeded into 6-well plates in serum-supplemented full MEM melanocyte and K-SFM keratinocyte medium for 24 h. The cells were switched to serum free medium (so-called starved) supplemented with L-18 (0.001-0.005%), L-19 (0.5-1.0%), L-20 (0.1-0.5%), L-21 (10 µg/ml), L-22 (0.1-1.0%) and L-23 (0.01-0.05 µg/ml) for 12 and 72 h. Controls included IBMX (100 µM) and niacinamide (10 µM). Cytotoxicity was assessed by cell death and cytopathologic change in morphology.

Approximately $1 \times 10^4$ EM and $2 \times 10^3$ FM55 melanoma cells were seeded into each well of a Lab-Tek® 8-well chamber slide and allowed to attach for 24 h. Cells were then washed 3-times with sterile PBS and supplemented with 350 µl of either fresh serum-free RPMI medium (melanoma cells) or starved serum-free and BPE-free melanocyte medium (EM) and incubated at 37° C. and 5% CO2 for 24 h. Cells were then washed with sterile PBS 3-times and incubated with IBMX $1 \times 10^4$ M at 37° C. and 5% CO2 for 12, 24, and 72 h. Cells were then gently washed 3-times with sterile PBS and fixed in ice-cold methanol for 10 minutes at −20° C. Slides were stored at −20° C. until immunocytochemistry was performed.

Melanin Assay: 500 µg/ml of synthetic melanin (Sigma, UK) was prepared in 1 M sodium hydroxide (NaOH) (BOH Ltd, UK) and dissolved in a sonicating water bath for 20 minutes. From this stock solution, various melanin standards were prepared in 1 M NaOH from 50 µg/ml to 1 µg/ml. The melanin standards were pipetted into a 96 well plate to produce a calibration curve for the assessment of melanin content in the test samples. 400 µl of 1 M NaOH was added to each cell pellet and dissolved on a heat block (100° C.) for 15 minutes. The pellets were vortexed vigorously and the solibulized pellet was pipetted into the same 96-well plate. The optical densities of the sample were read at 495 nm on a DYNEX REVELATION 4.02 program. Melanin content of each test sample was read from the calibration curve.

DOPA oxidase detection using non-denaturing SDS-PAGE for assessment of tyrosinase activity: Approximately $5 \times 10^5$ of EMc, and FM55 melanoma cells were seeded into three T75 flasks and were incubated at 37° C. and 5% CO2 overnight. The cells were prepared for SDS-PAGE and trans-blotted onto PVDF membranes. 70 µg of un-reduced protein extract without boiling was pipetted into the appropriate wells of 8% SDS-PAGE gels. The PVDF membrane containing the separated proteins was washed once in 1×PBS and then incubated at RT in 5 mM L-DOPA in 0.1 M sodium phosphate buffer for 3 hours with three changes of the L-DOPA. The L-DOPA reaction was stopped by washing the membrane in distilled water and the membrane was scanned.

Western blot analysis: EMc in a confluent T225 flask were trypsinised and seeded into T25 flask with full medium and allowed to attach overnight. 24 h before treatment the medium was replaced with starved medium for 24 h. Cells were washed 3-times with sterile PBS, and incubated in starved medium alone, or L-18 (0.001%), L-19 (1%), L-20 (0.5%), L-21 (10 µg/ml), L-22 (1%) and L-23 (0.05 µg/ml) for 12 and 72 h. Controls included IBMX (100 µM) and niacinamide (10 µM).

40 µg of total protein from each cell extract was electrophoresed in reducing SDS-8%-PAGE and blotted on PVDF membranes (Millipore Corporation, Bedford, Mass.). The membranes were blocked with 5% milk PBS/0.075% Tween 20 for 2 h at room temperature and were then probed with primary antibodies for overnight at 4° C. The molecular weight ladder (Magik Marker, Invitrogen) was incubated in 5% milk PBS/0.075% Tween 20 and the membrane strips were incubated with either 1 ml of 5% milk PBS/0.075% Tween 20 (negative control), or 1 ml of rabbit anti-Myo-X polyclonal antibody (1:200) in 5% milk PBS/0.075% Tween 20), 1 ml of rabbit anti-fascin (1:500) polyclonal antibody in 5% milk PBS/0.075% Tween 20) and 1 ml of goat anti-actin (1:1000) polyclonal antibody in 5% milk PBS/0.075% Tween 20) on a rocking platform overnight at 4° C.

After extensive washes the blots were incubated with horseradish peroxidise conjugated secondary antibodies for 2 h. The molecular weight ladder was then incubated with 1 ml of HRP-goat anti-human IgG (H+L) (Zymed, USA) (1:500) diluted in 5% milk PBS/0.075% Tween 20 and membrane strips were incubated in 1 ml of anti-rabbit IgG, horseradish peroxidase linked whole antibody (HRP) secondary antibody (Amersham Biosciences, UK) (1:700 diluted in 5% milk PBS/0.075% Tween 20) on a rocking platform for 2 hours at room temperature. The washing procedure was repeated and the membrane strips were incubated in LumiGLO® Reagent and Peroxide (BioLab Ltd, UK) for 2 minutes at room temperature. The chemiluminescent signal was detected by exposing the blot strips to Kodak XRA X-ray film (Kodak, UK) at various exposure times, followed by development in developing solution (Kodak, UK) until bands appeared, rinsed in tap water, fixed in the fixer (Kodak, UK) until the film turned blue, then rinsed with tap water and allowed to dry. The membrane was then labelled and scanned densitometric analysis a software (Image Master Total lab version 1.11).

Immunofluorescence staining: For EM:KC co-culture studies fully matched melanocytes (p4) and keratinocytes (p2) were seeded onto 8-well Lab-Tek® chamber slides at a cell density of $1 \times 10^4$ cells/well and in a ratio of 1 melanocyte to 10 keratinocytes. Co-cultures were maintained overnight (16 h) in a mixture of full K-SFM and MEM (co-culture medium) to allow cell attachment, followed by medium replenishment for a further 24 h. Cells were then fixed in ice-cold methanol for 10 min at −20° C., washed in PBS and then blocked with 10% donkey serum for the detection of protein expression in filopodia.

For double labelling experiments the first primary antibody, Myo-X (1:100) (Santa Cruz, Calif., USA) was applied overnight at 4° C., followed by incubation with FITC-conjugated secondary antibody (1:100) for 1 h at room temperature. The second primary antibody, either cytokeratin (1:100) (Abcam, Cambridge, UK) or β-Actin (1:100) (Santa Cruz, USA) or Fascin (1:100) (Santa Cruz, USA) or NKi/beteb (1:30) (Monosan) was applied for 1 h at room temperature followed by a TRITC-conjugated secondary antibody (1:100) (Jackson Immunoresearch Laboratories, Inc., West Grove, USA). DAPI (Vector Laboratories, Burlingame, Calif.) was used to stain nuclei. Images were captured with a cooled Hamamatsu digital camera using a 100× objective and post-processed using Paint Shop Pro (Jasc Software Ver. 7. CA, USA). Negative controls included the omission of primary antibody and replacement with non-immune serum from secondary antibody host and inclusion of secondary antibodies.

Quantitative analysis of melanosome transfer: Fully-matched epidermal melanocytes (p4) and epidermal keratinocytes (p2) from 4 normal individuals (i.e., F39; F67; F54; F52) were maintained in 8-well Lab-Tek® chamber slides at a total cell density of $2 \times 10^4$ cells/well and in a ratio of 1 melanocyte to 10 normal keratinocytes. The co-culture was maintained for further 24 h before washing 3-times with sterile PBS before incubation with starved medium alone, or L-18 (0.001%), L-19 (1%), L-20 (0.5%), L-21 (10 µg/ml), L-22 (1%) and L-23 (0.05 µg/ml) for 12 and 72 h. Controls included IBMX (100 µM) and niacinamide (10 µM). Cells were then processed for immunofluorescence staining with gp100 to assess melanosome transfer to keratinocytes.

Evaluation of melanosome transfer was performed by counting fluorescent gp100-positive spots within recipient keratinocytes in 5 random microscopic fields per well at 100× magnification (oil-immersion) in 3 independent experiments. To avoid counting melanin granules that may still be associated with melanocytes, we only counted gp100-positive spots within keratinocytes that were not in direct contact with melanocytes.

Knockdown of Myo-X using siRNA: A synthetic siRNA targeting human Myo-X (5'-CAGCGGTATAAGAGAAAT-CAA-3') (SEQ ID No 1) and a non-silencing control, consisting of siRNA that has no known homology with mammalian genes (5'-AATTCTCCGAACGTGTCACGT-3') (SEQ ID No 2) was obtained from Qiagen, Valencia, Calif. A day before siRNA treatment, $5 \times 10^5$ epidermal melanocytes per well were plated onto six-well plates at 50-60% confluency and incubated at 37° C. for 12 h. Cells were then treated for 12 h with a final concentration of 25 nM siRNA by using HiPer-Fect Transfection Reagent (Qiagen, Valencia, Calif.) following the manufacturer's instructions. Fluorescence microscopy was used to verify that approximately 100% of the cells (using non-silencing control labelled with alexa fluor 488 labels) had taken up the siRNA. At 12 h, the cells from each well were replated into 8-well Lab-Tek® chamber slides. For co-culture studies siRNA treated melanocytes were seeded with normal keratinocytes (passage 2) in 8-well Lab-Tek® chamber slides at a cell density of $2 \times 10^4$ cells/well and in a ratio of 1 siRNA treated melanocyte to 10 normal keratinocytes. At 24 h the co-culture were processed for double Immuno fluorescence staining with gp100 and cytokeratin or Myo-X to study of the influence of gene knockdown on melanosome transfer, and parallel samples were assayed by immunofluorescence staining and western blot analysis to verify gene knockdown. For another experiment these co-culture were treated with or without L-18-23 for 24 h.

Results/Discussion

Dose Selection of Plant Extracts L-18-23:

Cells were incubated with the plant extracts and modulators of pigmentation (IBMX and niacinamide) at a range of concentrations. Some doses resulted in cell death or abnormal change in cell morphology (e.g., vacuolation). The inventor showed that optimal L-18-23 active doses that were not associated with altered cell growth or morphology. These doses were therefore used for the remainder of the study.

Normal human epidermal keratinocyte culture (Female-67; p2) were treated for 72 h with L-18 (0.001%), L-19 (1%), L-20 (0.5%), L-21 (10 µg/ml), L-22 (1%) and LVMH-23 (0.05 µg/ml). Controls: Melanocytic modulators: IBMX (100 µM) and niacinamide (10 µM).

Normal human epidermal melanocyte culture (Female-67; p4) were treated for 72 h with L-18 (0.001%), L-19 (1%), L-20 (0.5%), L-21 (10 µg/ml), L-22 (1%) and L-23 (0.05 µg/ml). Controls: Melanocytic modulators: IBMX (100 µM) and niacinamide (10 µM).

Dose Selection for Experimental Design

| Plant Extracts | Final dose selection for study on MC-KC Co-culture |
| --- | --- |
| L-18 | 0.001% |
| L-19 | 1.0% |
| L-20 | 0.5% |
| L-21 | 10 µg/ml |
| L-22 | 1.0% |
| L-23 | 0.05 µg/ml |

Figure 2:
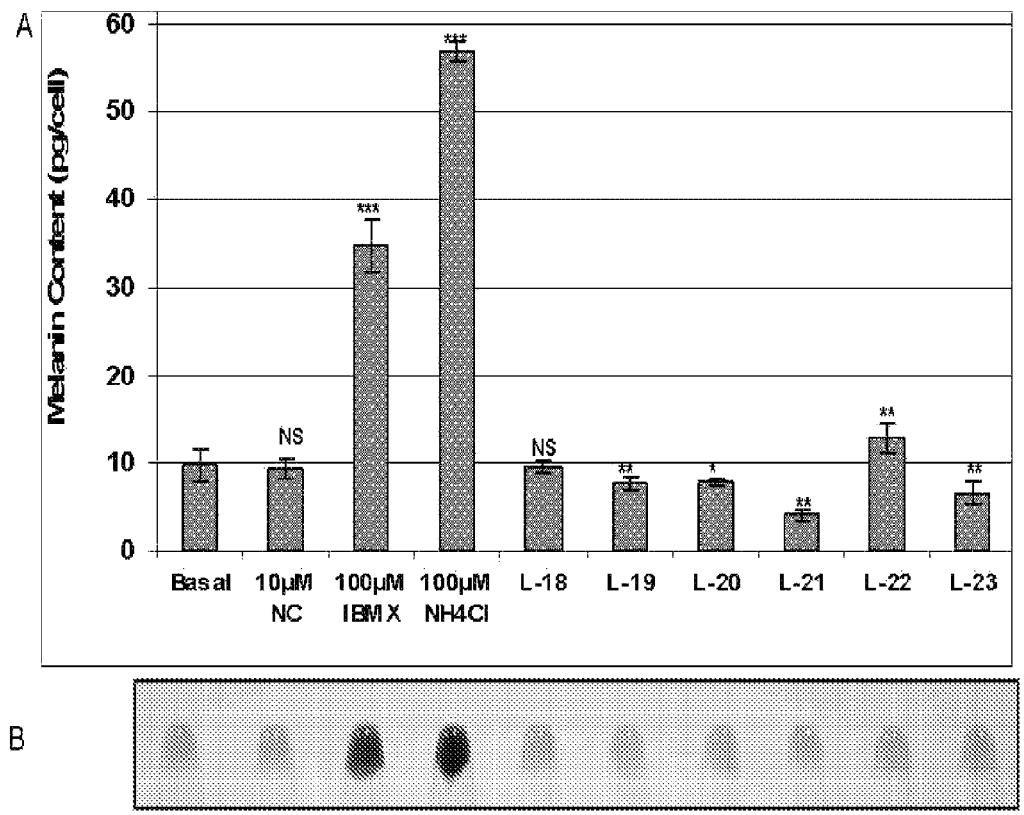
FIG. 2 shows the effect of plant extracts of the invention on melanogenesis in moderately-pigmented FM55 melanoma.

Effect of Plant Extracts L-18-23 on Melanogenesis:

Normal human epidermal melanocytes (F52; p5) and human melanoma (FM55) were treated for 72 h with L-18 (0.001%), L-19 (1%), L-20 (0.5%), L-21 (10 µg/ml), LVMH-22 (1%) and L-23 (0.05 µg/ml). In addition IBMX and NH4Cl (positive melanocytic modulators) and niacinamide (negative modulator) were used as controls. Visible change was not particularly evident in normal melanocyte due to their already high basal melanin levels (FIG. 1). By contrast, visible change was evident in melanoma cells basal melanin levels were low (FIG. 2). L-19, L-20, L-21 and L-23 significantly reduced melanin content compared with basal levels in both normal melanocytes and FM55 melanoma cells. L-22 however was associated with an increase in melanin content compared with basal levels. L-18 did not induce a significant change in these cells. Results are summarized in Table 1 and in FIGS. 1 & 2.

FIG. 1: Effect of Plant Extracts L-18-23 Actives on Melanogenesis in Normal Pigmented Human Melanocytes Normal human epidermal melanocytes (Female-52; p5) were treated for 72 h with L-18 (0.001%), L-19 (1%), L-20 (0.5%), L-21 (10 µg/ml), L-22 (1%) and L-23 (0.05 µg/ml). Controls: Melanocytic modulators: IBMX (100 µM), NH4Cl (100 µM), and niacinamide (10 µM).

(A) Melanin content was determined spectro-photometrically (475 nm) after sodium hydroxide solubilise (B) Visible change was not particularly evident in these cells due to their already high basal melanin levels. Results were expressed as change in melanin content (pg/cell) compared to unstimulated control levels. Means are ±SEM of 3 independent experiments with *P<0.05, P<0.01, *P<0.001. NS—Not Significant FIG. 2: Effect of Plant Extracts L-18-23 on Melanogenesis in Moderately-Pigmented FM55 Melanoma FM55 cells were treated for 72 h with L-18 (0.001%), L-19 (1%), L-20 (0.5%), LVMH-21 (10 µg/ml), L-22 (1%) and L-23 (0.05 µg/ml). Controls: Melanocytic modulators: IBMX (100 µM), NH4Cl (100 µM), and niacinamide (10 µM).

(A) Melanin content was determined spectrophotometrically (475 nm) after sodium hydroxide solubilisation. Cells with low basal melanin levels showed visible increases in melanogenesis after IBMX and NH4Cl stimulation.

(B). Results were expressed as the change in melanin content (pg/cell) compared to unstimulated control levels. Means are ±SEM of 3 independent experiments with *P<0.05, P<0.01, *P<0.001. NS—Not Significant.

TABLE 1

Changes in melanin levels after incubation with plant extracts L-18-23

|  | Basal | NC | IBMX | NH$_4$Cl | L-18 | L-19 | L-20 | L-21 | L-22 | L-23 |
|---|---|---|---|---|---|---|---|---|---|---|
| F52 EM | | | | | | | | | | |
| % change (pg/cell) | 0 (35.63) | −4.01 (34.2) | +74.57 (62.2) | +166.17 (94.83) | −4.57 (34.04) | −34.43 (23.36) | −15.66 (30.62) | −43.58 (20.2) | +31.60 (46.89) | −25.25 (26.62) |
| FM55 | | | | | | | | | | |
| % change (pg/cell) | 0 (9.92) | −5.94 (9.33) | +250.8 (34.8) | +478.82 (56.83) | −3.22 (9.62) | −21.90 (7.74) | −20.36 (7.92) | −58.65 (4.2) | +29.33 (12.82) | −33.20 (6.63) |

Figure 3:
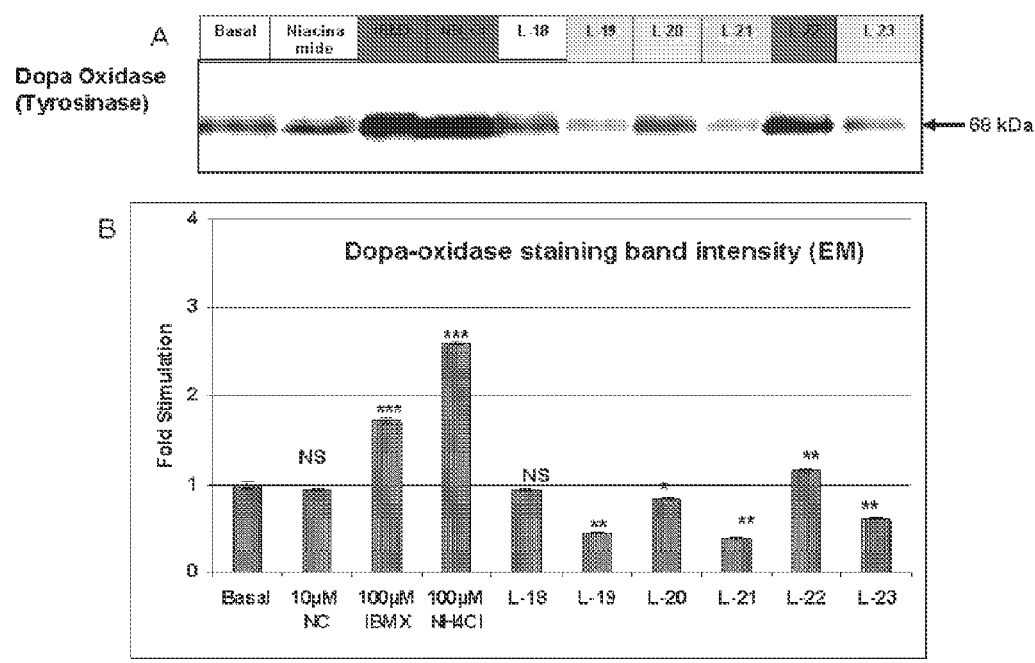
FIGS. 3A and 3B show the effect of plant extracts of the invention on tyrosinase activity in pigmented normal human melanocytes.
Figure 4:
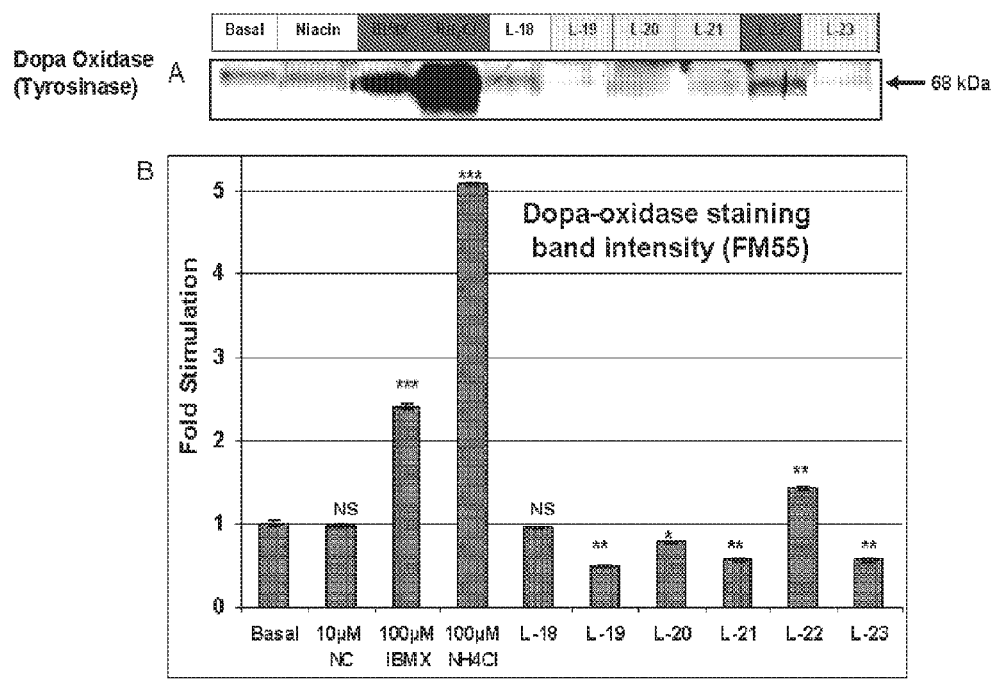
FIGS. 4A and 4B show the effect of plant extracts of the invention on tyrosinase activity in moderately pigmented FM55 melanoma.

Effect of Plants Extracts L-18-23 on Tyrosinase Activity:

Normal human epidermal melanocytes (F52; p5) and human melanoma (FM55) were treated for 72 h with L-18 (0.001%), L-19 (1%), L-20 (0.5%), L-21 (10 μg/ml), L-22 (1%) and L-23 (0.05 μg/ml). In addition IBMX and NH4Cl (positive melanocytic modulators) and niacinamide (negative modulator) were used as controls. IBMX and NH4Cl were associated with a dramatic increase in dopa oxidase activity of tyrosinase in both EM and FM55 cells (FIGS. 3 & 4). Of the L-18-23, L-19, L-20, L-21 and L-23 significantly reduced tyrosinase activity in both normal melanocytes and FM55 melanoma cells compared with basal levels (FIGS. 3 & 4). By contrast, L-22 however was associated with a significant increase in tyrosinase activity compared with basal levels, while L-18 did not induce any significant change. These results are summarized in Table 2.

FIG. 3: Effect of Plant Extracts L-18-23 on Tyrosinase Activity in Pigmented Normal Human Melanocytes Normal human epidermal melanocytes (Female-52; p5) were treated for 72 h with L-18 (0.001%), L-19 (1%), L-20 (0.5%), L-21 (10 μg/ml), LVMH-22 (1%) and L-23 (0.05 μg/ml). Controls: Melanocytic modulators: IBMX (100 μM), NH4Cl (100 μM), and niacinamide (10 μM).

(A) Protein extracts were electroblotted and membranes stained with L-DOPA for the estimation of tyrosinase activity.
(B) Densitometric scanning of band intensities and values were expressed as a fold increase compared to unstimulated control levels Means are ±SEM of 3 independent experiments with *P<0.05, P<0.01, *P<0.001. NS—Not Significant.

FIG. 4: Effect of Plant Extracts L-18-23 on Tyrosinase Activity in Moderately Pigmented FM55 Melanoma.

FM55 cells were treated for 72 h with L-18 (0.001%), L-19 (1%), L-20 (0.5%), L-21 (10 μg/ml), L-22 (1%) and L-23 (0.05 μg/ml). Controls: Melanocytic modulators: IBMX (100 μM), NH4Cl (100 μM), and niacinamide (10 μM).

(A) Protein extracts were electroblotted and membranes stained with L-DOPA for the estimation of tyrosinase activity.
(B) Densitometric scanning of band intensities and values were expressed as the fold increase compared to unstimulated control levels. Means are ±SEM of 3 independent experiments with *P<0.05, P<0.01, *P<0.001. NS—Not Significant.

Figure 5:
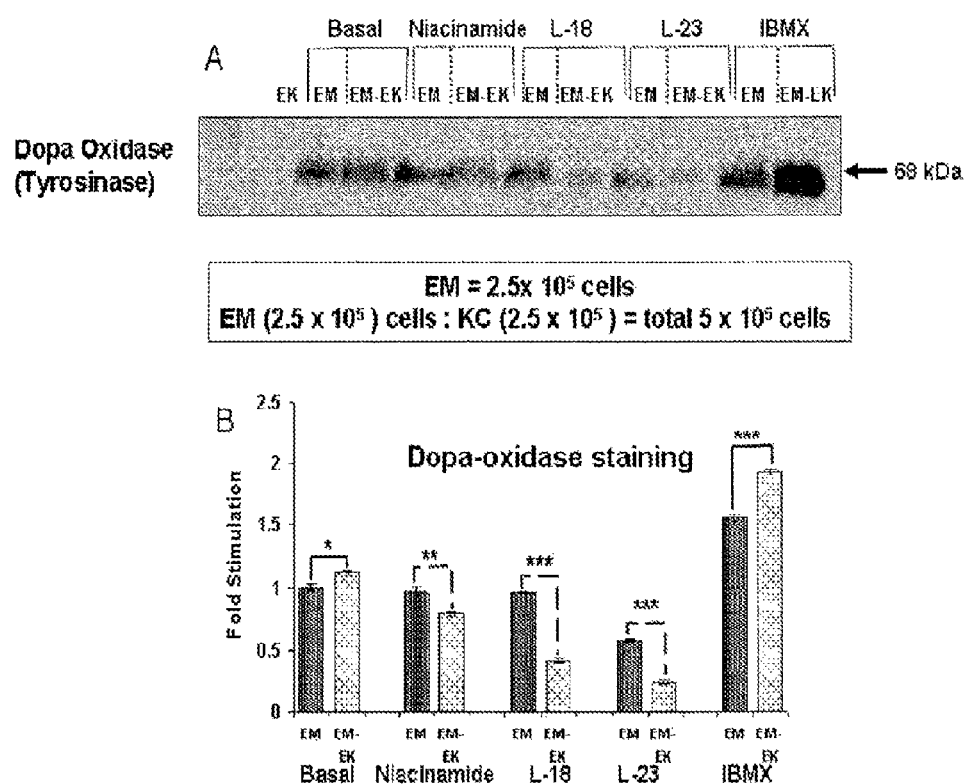
FIGS. 5A and 5B show the effect of plant extracts of the invention, IBMX and Niacinamide on tyrosinase activity in normal human melanocyte and keratinocyte co-culture.

However, results from EM as monoculture may not fully reflect paracrine influences from keratinocyte and thus may not fully reveal L-18-23 associated effects. Therefore, the above assessment for tyrosinase activity was repeated with two of the plant extracts; one which showed no change (L-18) and one with a significant decrease (L-23) in fully-matched EM:KC co-cultures. It was interesting to note that under co-culture conditions, L-18 now showed a significant decrease in dopa oxidase activity of tyrosinase (from −3.46% when on EM cells grown alone to −57.02% when co-cultured with matched KC). For L-23, a further decrease in dopa oxidase activity of tyrosinase was seen when in co-culture (i.e., from −41.16% in monoculture to −76.17% in co-culture) (FIG. 5, and Table 3). A similar positive and negative trend was also seen with IBMX and niacinamide respectively.

FIG. 5: Effect of Plant Extracts L-18 and L-23, IBMX and Niacinamide on Tyrosinase Activity in Normal Human Melanocyte and Keratinocyte Co-Culture (Note: Protein Loading was Normalized for Melanocyte Protein Only).

Normal human epidermal melanocyte culture (Female-52; p5) and matched co-culture F52 MC-KC were treated for 72 h with L-18 (0.001%), L-23 (0.05 μg/ml). Controls: Melanocytic modulators: IBMX (100 μM), and niacinamide (10 μM). Negative control lane: Keratinocytes only (A) Protein extracts were electroblotted and membranes stained with L-DOPA for the estimation of tyrosinase activity.
(B) Densitometric scanning of band intensities and values were expressed as the fold increase compared to unstimulated control levels. Means are ±SEM of 3 independent experiments with *P<0.05, P<0.01, *P<0.001.

TABLE 2

Changes in tyrosinase activity after incubation with plants extracts L-18-23

|  | Basal | NC | IBMX | NH$_4$Cl | L-18 | L-19 | L-20 | L-21 | L-22 | L-23 |
|---|---|---|---|---|---|---|---|---|---|---|
| F52 EMc | | | | | | | | | | |
| % change | 0 | −4.58 | +72.47 | +159.63 | −6.17 | −55.23 | −13.76 | −60.55 | +16.50 | −39.44 |
| FM55 | | | | | | | | | | |
| % change | 0 | −3.31 | +141.72 | +408.27 | −5.29 | −50.37 | −22.15 | −42.54 | +43.54 | −42.88 |

TABLE 3

Changes in EM tyrosinase activity on EM:KC co-cultures after incubation with plants extracts L-18 and L-23

| | Basal | | | | | | | | | |
|---|---|---|---|---|---|---|---|---|---|---|
| | | EM- | NC | | L-18 | | L-23 | | IBMX | |
| | EM | EK | EM | EM-EK | EM | EM-EK | EM | EM-EK | EM | EM-EK |
| % Change in EM Tyrosinase Activity vs Basal EM level (i.e. 0) | 0 | +12.16 | −2.12 | −20.50 | −3.46 | −57.02 | −41.16 | −76.17 | +56.51 | +93.41 |
| % Change in EM Tyrosinase Activity of stimulated EM vs stimulated EM-EK) level (i.e. 12.16) | | +12.16 | | −18.84 | | −56.47 | | −57 | | +23.57 |

Figure 6:
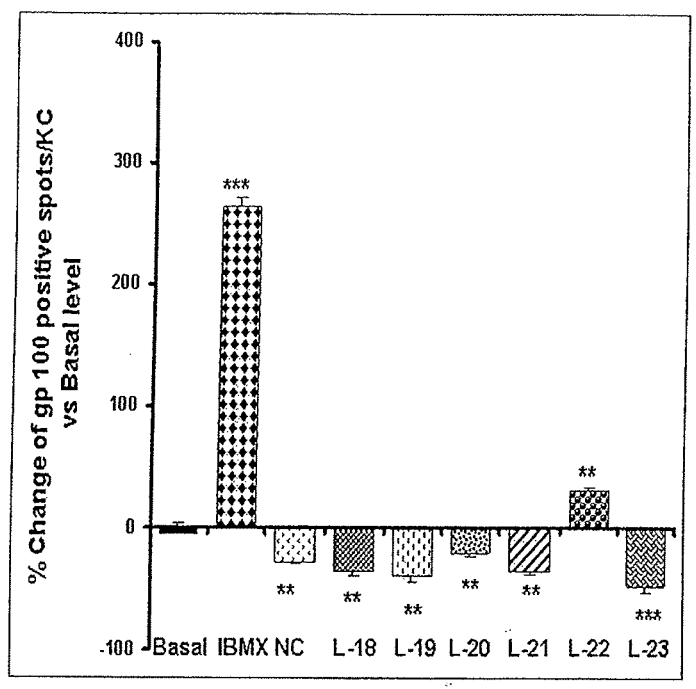
FIG. 6 shows results of quantitative analysis of melanosome transfer after incubation with the plant extracts of the invention.

Quantitative Analysis of gp100-Positive Melanosome Transfer Using Plants Extracts L-18 and L-23:

Gp100 immunostaining provides a powerful tracking method for the global assessment of melanin transfer to keratinocytes, and for the evaluation of melanocyte phenotype modulators (Singh et al., 2008). Double immunolabelling (NKi/beteb and anti-cytoskeleton antibody) of the EM:KC co-cultures after treatment with all L-18-23, a phosphodiesterase inhibitor IBMX (i.e., cAMP inducer) and niacinamide all revealed clear changes in the number of fluorescent green gp100-positive melanin granules in keratinocytes (FIG. 6). In this assay melanosome transfer from melanocytes to matched keratinocytes under basal (i.e., unstimulated) conditions was determined at an average of 27.3 gp100-positive spots per keratinocyte. However, this was increased almost 4-fold after 24 h stimulation of co-cultures with IBMX to 99.5 gp100-positive spots per keratinocyte. Conversely, niacinamide reduced melanosome transfer by 28% (19.6 gp100-positive spots per keratinocyte; p<0.01; a result that correlates with its clinical use as a lightener of cutaneous pigmentation (Hakozaki et al, 2002; Greatens et al., 2005).

L-18, L-19, L-20, L-21 and L-23 all significantly reduced melanosome transfer as evidenced by a reduction of melanosome transfer compare to unstimulated control. By contrast, an increase in melanosome transfer to keratinocytes was observed when co-cultures were stimulated with L-23), compared with unstimulated basal levels.

FIG. 6: Quantitative Analysis of Melanosome Transfer after Incubation with Plants Extracts L-18-23 (Table 4)

Melanocyte-keratinocyte matched co-cultures (Female-39) were treated for 24 h with L-18 (0.001%), L-19 (1%), L-20 (0.5%), L-21 (10 µg/ml), L-22 (1%) and L-23 (0.05 µg/ml) along with parallel known melanocytic modulators (IBMX (100 µM) and niacinamide (10 µM). Double-immunolabelling with anti-gp100 antibody (green) and anti-actin antibody (red) revealed clear changes in the number of fluorescent spots transferred to keratinocytes. Quantification of transferred melanosomes taken from 5 randomly-selected microscopic fields (total 20 cells per field) for each of the different treatment groups. Values were expressed as the percentage increase in the number of gp100-positive spots per keratinocyte compared to unstimulated control levels. Means are ±SEM of 4 independent experiments with P<0.01, *P<0.001.

TABLE 4

| gp100+ Spots/KC | | | | | | | | |
|---|---|---|---|---|---|---|---|---|
| 27.3 ± 0.9 | 99.5 ± 5.4 | 19.6 ± 0.7 | 17.8 ± 1.5 | 16.5 ± 1.9 | 21.7 ± 0.8 | 17.6 ± 0.9 | 36.0 ± 2.9 | 14.5 ± 2.2 |
| % Change of Melanin Transfer vs Basal | +264 | .28 | .34 | .39 | .20 | .35 | +31 | .47 |

Effect of Plant Extracts L-18-23 on Myo-X Expression in Normal Human Melanocytes.

Double immunolabeling with antibodies against the Myo-X (Date not shown) and gp100 revealed prominent Myo-X expression in EM cell periphery and dendritic tips. Myo-X was also detected in EM filopodia. We have found that IBMX increased the expression of Myo-X and the overall number of filopodia (as suggested by total number of yellow spots beyond EM dendritic tips). IBMX also enhanced Myo-X localization in EM filopodia compared with untreated cells in. By contrast, Myo-X expression was significantly down-regulated in EM by L-18, L-19, L-20, L-21 and L-23, while it was upregulated by L-22 alone. The localization of Myo-X within EM filopodia was also significantly reduced by these plant extracts.

Western blot analysis of EM (F39) stimulated for 12 h by IBMX (100 µM) showed a 3-fold increase in Myo-10 expression as compared with the untreated controls (FIG. 7A,B). By contrast, the melanosome transfer inhibitor niacinamide (10 µM) reduced Myo-X expression by 60%. All L-18-23 significantly down-regulated EM Myo-X expression (FIG. 7A,B), with the exception of L-22.

Figure 7:
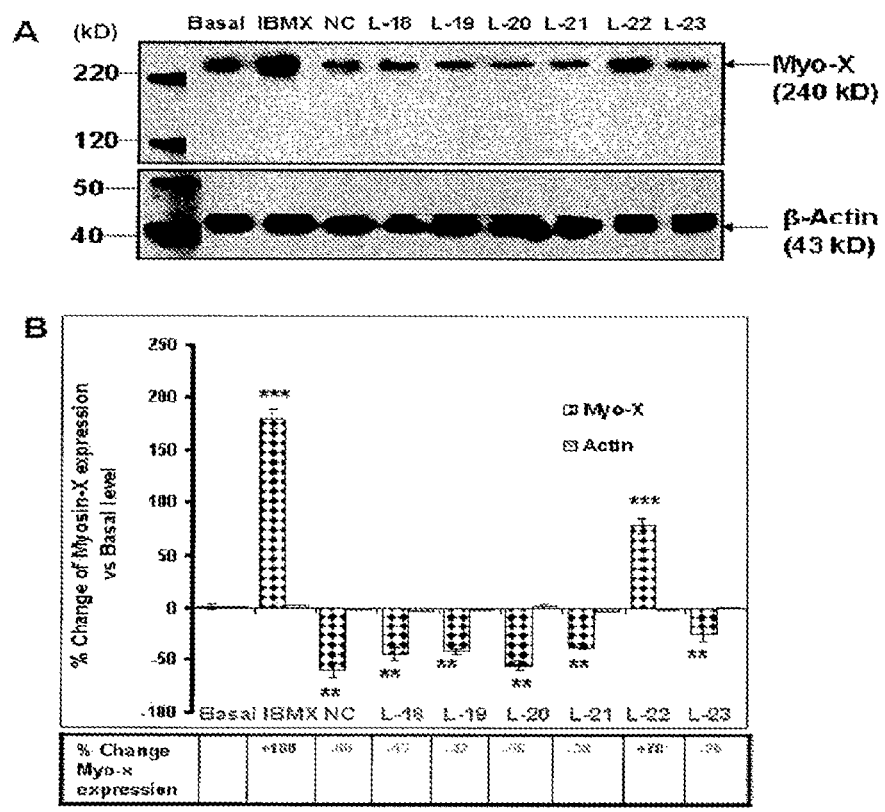
FIGS. 7A and 7B show the effect of plant extracts of the invention on Myo-X protein expression by Western Blotting in normal human melanocytes.

FIG. 7: Effect of Plant Extracts L-18-23 on Myo-X Protein Expression by Western Blotting in Normal Human Melanocytes Normal human epidermal melanocyte cultures (F39-EM) were treated for 12 h with L-18 (0.001%), L-19 (1%), L-20 (0.5%), L-21 (10 µg/ml), L-22 (1%) and L-23 (0.05 µg/ml). Controls: IBMX (100 µM) and niacinamide (10 µM).

(A) Cell extracts were analyzed by Western blotting using anti-Myo-X and anti-β-actin as a loading control.

(B) Densitometric analysis of Myo-X and actin band intensities expressed as percentage change compared to unstimulated controls. Means are ±SEM of 3 independent experiments with P<0.01, *P<0.001.

The Knockdown of Myo-X Expression in Epidermal Melanocytes Inhibits Melanosome Transfer to Epidermal Keratinocytes The role of Myo-X in melanosome transfer was investigated by using synthetic siRNA for 12 h against human Myo-X and non-silencing control siRNA. Myo-X silencing in melanocyte cells was assayed by western blot analysis. This inhibition was also confirmed by immunofluorescence, which also showed that the expression of Myo-X was almost completely inhibited compared to the non-silencing control siRNA. Double-immunolabelling of the Myo-X-silenced melanocytes with anti-gp100 antibody revealed the absence of filopodia as evidenced by the lack of gp100-positive melanosome around the melanocyte tips. Melanocyte treated with non-silencing control siRNA showed prominent Myo-X and gp100 in the filopodial region.

We were keen to determine, whether endogenous Myo-X expression is a requirement for melanosome transfer via filopodia in melanocyte. In order to test the involvement of Myo-X in melanin transfer, Myo-X-silenced melanocytes and non-silenced melanocytes were used to establish the MC-KC co-culture for 24 h. Double Immunolabelling of this co-culture with anti-gp100 antibody and anti-Myo-X clearly showed the inhibition in the number of fluorescent spots transferred to keratinocytes cultured with Myo-X-silenced melanocytes. Double-immunolabelling with anti-gp100 antibody and anti-cyokeratin revealed clear changes in the number of fluorescent spots (representing melanin granule) transferred to keratinocytes.

Figure 8:
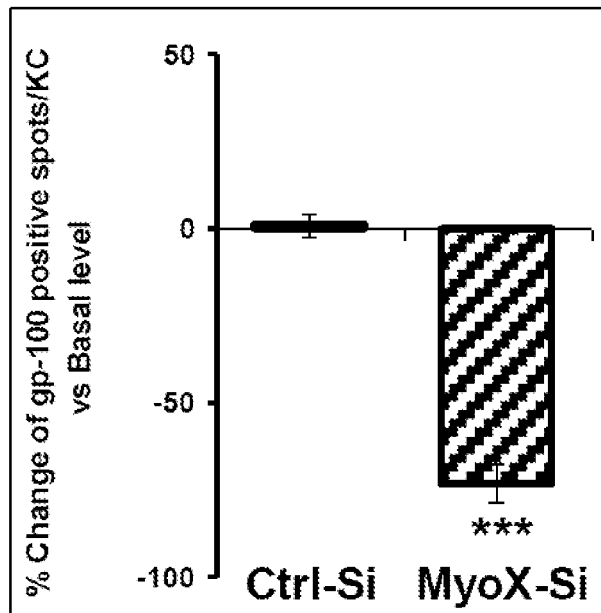
FIG. 8 shows results of quantitative analysis of melanosome transfer after knockdown of Myo-X expression of epidermal melanocytes in epidermal melanocytes-keratinocytes co-culture.

Using this assay the rate of melanosome transfer from melanocytes to keratinocytes with non-silencing control siRNA conditions was determined (FIG. 8). This level of melanosome transfer was reduced by 80% in Myo-X-silenced melanocytes cultured with normal keratinocyte cells for 24 h (FIG. 8). This is the first demonstration of a physiological role of Myo-X in the successful transfer of melanosomes from melanocytes to keratinocytes.

In the following examples, the percentages are given by weight from the total weight of the composition. The amount of plant extracts is expressed as dry weight.

EXAMPLE 1

Cosmetic Powder for Lightening the Facial Complexion

| | |
|---|---|
| *Cyathea cumingii* leaf extract | 0.5% |
| Microcellulose | 20.0% |
| Sodium lauryl sulphoacetate | 15.0% |
| Fragrance, dyes, preserving agents | qs |
| Talc | qs 100% |

This powder allows cleansing of the skin, and also makes it possible, through regular use for a few days, to lighten the complexion. It can be applied to the facial skin once or twice a day.

EXAMPLE 2

Depigmenting Cosmetic Day Cream in Emulsion-Gel Form

| | |
|---|---|
| *Secale cereale* seed extract | 0.1% |
| Glycerol | 5.0% |
| caprylic/capric/succinic triglycerides | 5.0% |
| Octyl methoxycinnamate | 1.0% |
| Copolyol dimethicone | 0.5% |
| Acrylates/C10-30 alkyl acrylate crosspolymer | 0.5% |
| Neutralising agent | as needed. |
| Preservation agents, odorant, colouring agents | as needed. |
| Water | qs 100% |

Some individuals subjected to more or less intense irradiation due to daylight, or even direct sunlight, would like to keep a light skin and avoid the appearance of pigmenting spots.

The use of the emulsion-gel defined above provides the means of achieving this purpose. This composition is usually applied on the face in the morning. It is equally effective for preventive and remedial action on regular or irregular pigmentation of the face.

EXAMPLE 3

SPF 30 Protective Fluid Preventing Pigmentation Spots

| | |
|---|---|
| *Thassiora pseudonana* extract | 0.01% |
| Volatile pentacyclomethicone | 49.0% |
| Titanium dioxide | 15.0% |
| Octyl methoxycinnamate | 7.5% |
| Glycerine | 5.0% |
| Phenyltrimethicone | 5.0% |
| Copolyol dimethicone | 3.0% |
| Polymethylmethacrylate | 2.5% |
| Butyl methoxydibenzoyle methane | 1.0% |
| Neutralising agent, odorant, preservation agents, antioxydisers | as needed. |
| Water | qs 100% |

The protective fluid is used to prevent the appearance of pigmentation spots in persons subject to this phenomenon, before exposure to intense solar radiation. It should be noted that the presence of a high concentration in the solar filter compensates for the reduction in natural protection due to the drop in the melanin content.

EXAMPLE 4

Dermatological Cream for the Treatment of Skin Hyperpigmentations of Pathological or Trauma-Based Origin

| | |
|---|---|
| *Cyathea cuminghii* leaf extract | 0.3% |
| Glyceryl stearate + PEG-100 stearate | 5.0% |
| Hydrogenated polyisobutene | 4.0% |
| Magnesium ascorbyl phosphate | 3.0% |
| Glyceryl tricaprylate/caprate | 3.0% |
| Squalane | 3.0% |
| Glycerol | 2.0% |
| Beeswax | 1.5% |
| Cetearyl octanoate | 1.5% |
| Cetyl alcohol | 1.0% |
| Stearyl alcohol | 1.0% |
| Dimethicone | 1.0% |
| Xanthan gum | 0.3% |
| Ethylenediaminetetraacetic acid | 0.2% |
| Citric acid | 0.1% |
| Sodium citrate | 0.1% |
| Neutralizing agent, fragrance, preserving agents | qs |
| Water | qs 100% |

The use of this cream makes it possible to reduce skin hyperpigmentations of pathological or trauma-based origin. This cream also makes it possible to reduce the colour contrast at the periphery of depigmented areas in the case of vitiligo.

EXAMPLE 5

Cosmetic Face Lotion for Lightening the Complexion

| | |
|---|---|
| *Thalassiosira pseudonana* | 0.01% |
| Ethyl alcohol | 30.0% |
| PPG-3 myristyl ether | 5.0% |
| Glycerol | 2.0% |
| Carbomer | 0.2% |
| Polysorbate 20 | 0.2% |
| Neutralizing agent, fragrance, preserving agents | qs |
| Water | qs 100% |

This lotion for lightening the complexion is used after removing make-up from the skin and cleansing the latter.

EXAMPLE 6

Cosmetic Facial Lightening Serum

| | |
|---|---|
| *Secale cereale* (Rye) seed extract | 0.2% |
| Glycerol | 2% |
| Tetrasodium EDTA | |
| Citric acid | qs desired pH |
| Trisodium citrate | |
| Xanthan gum | 0.3% |
| Polyacrylamide, C13.14 isoparaffin, laureth-7 | 0.5% |

-continued

| | |
|---|---|
| Dimethicone copolyol | 0.3% |
| Fragrance, dye, preserving agent | qs |
| Water | qs 100% |

A drop of this very concentrated serum composition is applied to the face, generally before the application of a face cream. This serum is normally used as treatments of one to two weeks so as to obtain or maintain a lightening of the complexion.

EXAMPLE 7

Cosmetic Lotion for Lightening Body Hair

| | |
|---|---|
| *Thalassiosira pseudonana* extract | 0.01% |
| Panthenyl ethyl ether | 0.5% |
| DL-α-tocopheryl acetate | 0.2% |
| Polysorbate 60 | 1% |
| Fragrance | 0.2% |
| Glycerol | 0.5% |
| Dye | qs |
| Water | qs 100% |
| Alcohol | 50% |

This lotion is applied to the areas with hair that are to be lightened, in particular the arms, for the amount of time sufficient to obtain gradual lightening of the hairs.

EXAMPLE 8

Cosmetic Anti-Spot Gel-Cream for the Hands

| | |
|---|---|
| Caprylic/capric diglyceryl succinate | 6% |
| Octyl octanoate | 2.5% |
| Octyl methoxycinnamate | 6% |
| *Cyathea cumingii* leaf extract | 0.3% |
| Phenyltrimethicone | 2.5% |
| Benzophenone-3 | 0.5% |
| Sodium hyaluronate | 0.1% |
| Xanthan gum | 0.2% |
| Acrylates/C10.30 alkyl acrylate copolymer | 0.5% |
| Glycerol | 2% |
| PEG 150 | 3% |
| Neutralizing agents, dyes, fragrance, preserving agents | qs |
| Purified water | qs 100% |

This cream must be applied directly to the spots (solar and/or senile lentigo) on the hands, so as to reduce the colouration of said spots.

EXAMPLE 9

Dermatological Solution for Treating Pathological Hyper Pigmentation

| | |
|---|---|
| *Secale cereale* seed extract | 0.2% |
| Volatile pentacyclomethicone | 49.0% |
| Titanium dioxide | 15.0% |
| Octyl methoxycinnamate | 7.5% |
| Glycerine | 5.0% |

| | |
|---|---|
| Phenyltrimethicone | 5.0% |
| Copolyol dimethicone | 3.0% |
| Polymethylmethacrylate | 2.5% |
| Butyl methoxydibenzoylmethane | 1.0% |
| Neutralising agent, Odorant, Preservation agents, antioxidants | as needed |
| Water | Qs 100% |

This serum is applied to the skin daily for the treatment of persons suffering from regional hyper pigmentation.

EXAMPLE 10

Hair Tonic Lotion for Depigmenting Hair

| | |
|---|---|
| *Secale cereale* seed extract | 0.2% |
| 3-Methylxantine | 0.03% |
| Alcohol | 30.0% |
| Perfumed aqueous excipients with perfume solubilizer | Qs 100.0% |

EXAMPLE 11

Tanning Sun Cream

| | |
|---|---|
| Hydrolysed soy flour (soy seed pericarp extract) | 0.3% |
| Isocetyl stearate | 8.0% |
| Hydrogenated groundnut oil | 10.0% |
| Lanolin oil | 3.5% |
| Cetyl alcohol | 5.0% |
| Stearyl alcohol | 2.5% |
| Light liquid paraffin | 10.0% |
| Neutralized phosphoric acid monoester of oxyethylenated cetyl alcohol | 3.0% |
| Octylmethoxy cinnamate | 5.0% |

This phase is emulsified with an aqueous phase qs 100% containing:

| | |
|---|---|
| Pantothenol | 0.1% |
| Preservatives | 0.2% |

EXAMPLE 12

Lotion for Strengthening Natural Sun Protection

| | |
|---|---|
| Alcohol | 42.50% |
| Propylene glycol | 3.00% |
| Menthol | 0.05% |
| Hydroxypropyl methyl cellulose | 1.5% |
| Hydrolysed soy flour | 0.2% |
| Perfumed aqueous excipients | Qs 100.0% |

This lotion is applied locally, preferably twice a day, every day for 3 to 8 days preceding prolonged exposure to the sun. The daily applications can be continued during the period of exposure.

EXAMPLE 13

Hair Tonic Lotion for Pigmenting Gray Hair

| | |
|---|---|
| Hydrolysed soy flour (soy seed pericarp extract) | 0.10% |
| 3-Methylxanthine | 0.03% |
| Alcohol | 30.0% |
| Perfumed aqueous excipients with perfume solubilizer | Qs 100.0% |

This lotion can be applied to the hair and scalp twice a day for a vigorous treatment intended for rapidly reducing the appearance of white hair.

EXAMPLE 14

Dermatological Gel Intended for Promoting the Pigmentation of the Skin

| | |
|---|---|
| Hydrolysed soy flour | 0.10% |
| Ethanol | 0.03% |
| Distilled water | 30.0% |
| Gelling excipient, with 1.25% Carbopol 940 ® gel | Qs 100.0% |

REFERENCES

Bohil A B, Robertson B W, Cheney R E (2006). Myosin-X is a molecular motor that functions in filopodia formation. PNAS 103: 12411-12416.

Kawabata M, Imamura T, Miyazono K (1998) Signal transduction by bone morphogenetic proteins. *Cytokine Growth Factor Rev.* 9, 49-61.

Scott G, Leopardi S, Printup S, Madden B C (2002). Filopodia are conduits for melanosome transfer to keratinocytes. J Cell Sci: 115: 1441-1451.

Singh S K, Nizard C, Kurfurst R, Bonte F, Schnebert S, Tobin D J (2008). The silver ocus product (Silv/gp100/Pmel17) as a new tool for the analysis of melanosome transfer in human melanocyte—keratinocyte co-culture. Exp Dermatol. 17 (5):418-26.

L. R. SNYDER: Classification of the solvent properties of common liquids; Journal of Chromatography, 92 (1974), 223-230.

Sousa, A. D. & Cheney, R. E. (2005). Myosin-X: A Molecular Motor at the Cell's Fingertips *Trends Cell Biol.* 15, 533-539.

The invention claimed is:

1. A method of assessing the ability of a substance to modulate the transfer of melanin for a melanocyte to a keratinocyte, the method comprising the steps of:
   a)—providing a test substance;
   b)—providing a cell expressing Myo-X; and
   c)—determining the ability of the test substance to modulate the expression or the activation of Myosin-X (Myo-X) in the cell.

2. The method of claim 1, wherein the cell expressing Myo-X is a melanocyte or a keratinocyte.

3. The method of claim 1, comprising comparing the expression or activation of Myo-X in a cell treated with a test substance with the expression or the activation of Myo-X in a control cell.

4. The method according to claim 1, wherein determining the ability of the test substance to modulate the expression or the activity of Myo-X includes:
   measuring the amount of Myo-X protein in or on the cell;
   determining the amount of a precursor in the synthesis of Myo-X protein; or
   measuring the melanosome transfer level in the cell.

5. A method of selecting an active substance capable to enhance skin or hair pigmentation comprising:
   assessing the ability of said substance to modulate the transfer of melanin according to steps a) to c) of the method of claim 1,
   selecting the substance capable to increase the expression or the activation of MyoX.

6. A method of selecting a substance capable to reduce skin or hair pigmentation comprising:
   assessing the ability of said substance to modulate the transfer of melanin according to steps a) to c) of the method of claim 1,
   selecting the substance capable to decrease the expression or the activation of MyoX.

7. A method according to claim 1, wherein the assessed substance is a plant extract.

* * * * *